(12) United States Patent
Splinter et al.

(10) Patent No.: US 10,210,960 B2
(45) Date of Patent: Feb. 19, 2019

(54) X-RAY INSPECTION SYSTEM X-RAY RADIATION SHIELDING CURTAINS

(71) Applicant: Analogic Corporation, Peabody, MA (US)

(72) Inventors: Patrick Splinter, Middleton, MA (US); Steven Weed, Marblehead, MA (US)

(73) Assignee: Analogic Corporation, Peabody, MA (US)

( * ) Notice: Subject to any disclaimer, the term of this patent is extended or adjusted under 35 U.S.C. 154(b) by 143 days.

(21) Appl. No.: 15/114,206

(22) PCT Filed: Jan. 31, 2014

(86) PCT No.: PCT/IB2014/058720
§ 371 (c)(1),
(2) Date: Jul. 26, 2016

(87) PCT Pub. No.: WO2015/114411
PCT Pub. Date: Aug. 6, 2015

(65) Prior Publication Data
US 2016/0372223 A1 Dec. 22, 2016

(51) Int. Cl.
*G21F 3/00* (2006.01)
*G01N 23/04* (2018.01)
*G01V 5/00* (2006.01)

(52) U.S. Cl.
CPC .............. *G21F 3/00* (2013.01); *G01N 23/04* (2013.01); *G01V 5/0016* (2013.01); *G01N 2223/643* (2013.01)

(58) Field of Classification Search
CPC .............. G01N 2223/643; G01N 23/04; G01V 5/0016; G21F 3/00
See application file for complete search history.

(56) References Cited

U.S. PATENT DOCUMENTS 6,058,159 A     5/2000  Conway et al.
7,050,536 B1 *  5/2006  Fenkart ................ G01V 5/0016
                                                          378/57

(Continued)

FOREIGN PATENT DOCUMENTS

DE     102008031080 A1    1/2010
JP        2002082199 A    3/2002

OTHER PUBLICATIONS

International Search Report for PCT/IB2014/058720 published as WO2015/114411 dated Aug. 6, 2015.
(Continued)

*Primary Examiner* — Mark R Gaworecki
(74) *Attorney, Agent, or Firm* — TraskBritt (57) ABSTRACT

A transport apparatus of an X-ray inspection system includes an inspection region with an entrance and an exit. The transport apparatus further includes a loading region disposed at the entrance of the inspection region, the loading region. The loading region includes a first set of X-ray attenuating curtains and a first curtain mover, which moves the curtains of the first set of X-ray attenuating curtains into and out of the loading region between areas that support objects for inspection. The transport apparatus further includes a conveyor device which moves an object for inspection residing in one of the areas from the loading region to the inspection region for inspection.

23 Claims, 6 Drawing Sheets

(56) References Cited

U.S. PATENT DOCUMENTS

| | | |
|---|---|---|
| 7,062,011 B1 | 6/2006 | Tybinkowski et al. |
| 7,072,434 B1 | 7/2006 | Tybinkowski et al. |
| 7,151,817 B1 | 12/2006 | Abraham et al. |
| 7,384,194 B2 | 6/2008 | Gatten |
| 7,667,215 B2 | 2/2010 | Hargrove, Jr. |
| 7,706,507 B2 | 4/2010 | Williamson et al. |
| 2005/0185757 A1 | 8/2005 | Kresse |
| 2013/0114788 A1 | 5/2013 | Crass |

OTHER PUBLICATIONS

International Written Opinion received for PCT Patent Application No. PCT/IB2014/058720, dated Aug. 8, 2014, 6 pages.
European Office Action received for European Application No. 14708325.7, dated Nov. 21, 2017, 6 pages.
European Office Action received for European Application No. 14708325.7, dated Jul. 9, 2018, 3 pages.
Chinese Third Office Action for Chinese Application No. 201480076607.6, dated May 31, 2018, 26 pages.
Chinese Second Office Action for Chinese Application No. 201480076607.6, dated Jan. 10, 2018, 15 pages.
Chinese First Search for Chinese Application No. 201480076607.6, dated Jun. 13, 2017, 1 page.
Chinese First Office Action for Chinese Application No. 201480076607.6, dated Jun. 26 2017, 26 pages.
Chinese Third Office Action for Chinese Application No. 201480076607.6, dated Oct. 25, 2018, 12 pages.

\* cited by examiner

X-RAY INSPECTION SYSTEM X-RAY RADIATION SHIELDING CURTAINS

RELATED APPLICATION

This application is a national filing of PCT application Serial No. PCT/IB2014/058720, filed Jan. 31, 2014 published as WO2015/114411 on Aug. 6, 2015. This application claims priority to PCT application Serial No. PCT/IB2014/058720, published as WO2015/114411 on Aug. 6, 2015.

TECHNICAL FIELD

The following generally relates to X-ray inspection system X-ray radiation shielding curtains and more particularly to an entrance and/or an exit port X-ray radiation shielding curtain of an X-ray shielded transport apparatus of an X-ray inspection apparatus.

BACKGROUND

An X-ray inspection system, such as a luggage and/or baggage X-ray based inspection system at an airport security checkpoint and/or other location, includes a transport apparatus (e.g., a conveyor belt) that transports an object for inspection from a first or loading location to a second or inspection location, where it is exposed to X-rays and imaged by an imaging apparatus, and then to a third or unloading location where the scanned or inspected object can be retrieved.

X-rays include ionizing radiation, and human exposure to ionizing radiation may cause damage to living tissue, which can result in mutation, radiation sickness, cancer, and death. As such, the transport apparatus has included X-ray shielding tunnels, inside of which the conveyor belt moves the object from the loading location to the inspection location and from the inspection location to the unloading location, with static vertical strips of an X-ray attenuating material such as lead at entrance and exit ports of the X-ray shielding tunnels.

As an object for inspection traverse the entrance port, the object (and/or a container carrying the object) physically contacts and displaces the static vertical strips. Unfortunately, this temporarily reduces the X-ray shielding, allowing X-rays to leave through the entrance port. Likewise, when the object traverses the exit port, the object (and/or the container carrying the object) physically contacts and displaces the static vertical strips. Again, unfortunately, this temporarily reduces the X-ray shielding, allowing X-rays to leave through the exit port.

Furthermore, as the object moves through the static vertical strips, friction between the object (and/or the container) may cause the object (and/or the container) to move in a manner which results in the object (and/or the container) becoming jammed in the X-ray shielding tunnel. Furthermore, when multiple objects are serially transported in the tunnel in different transporting areas and individually inspected, it may not be readily easy to ascertain when a particular object of a subject has moved to the unloading location where the subject can retrieve the object.

SUMMARY

Aspects of the application address the above matters, and others.

In one aspect, a transport apparatus of an X-ray inspection system includes an inspection region with an entrance and an exit. The transport apparatus further includes a loading region disposed at the entrance of the inspection region, the loading region. The loading region includes a first set of X-ray attenuating curtains and a first curtain mover, which moves the curtains of the first set of X-ray attenuating curtains into and out of the loading region between areas that support objects for inspection. The transport apparatus further includes a conveyor device which moves an object for inspection residing in one of the areas from the loading region to the inspection region for inspection.

In another aspect, a method includes deploying a first X-ray attenuating shield between an object receiving area in a loading region and an entrance of an inspection region. The method further includes translating the first X-ray attenuating shield in coordination with the object receiving area. The method further includes receiving an object to inspect in the object receiving area. The method further includes deploying a second X-ray attenuating shield on an opposing side of the object receiving area. The method further includes translating the first and second X-ray attenuating shields in coordination with the object receiving area of an object loading region. The method further includes removing the first X-ray attenuating shield. The method further includes moving the object to inspect into an inspection region where the object is scanned with an imaging device.

In another aspect, an X-ray inspection system includes a transport apparatus that moves an object from a loading region through an X-ray inspection region to an unloading region, in which a set of moving X-ray attenuating curtains, which moves in synchronization with the object, always blocks X-ray generated by an X-ray source at the X-ray inspection region from leaving the loading region and the unloading region.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
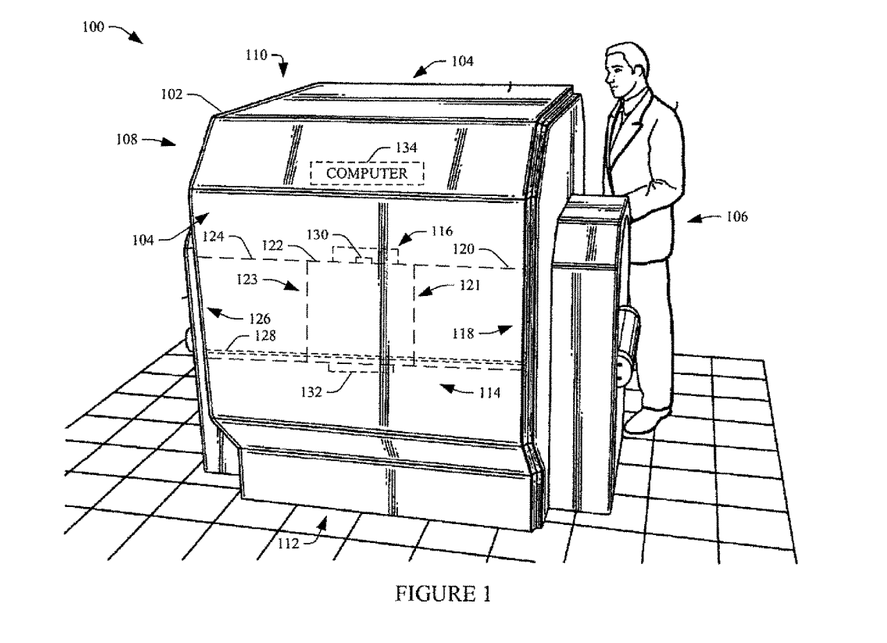
FIG. 1 schematically illustrates a side perspective view of an example inspection system.
Figure 2:
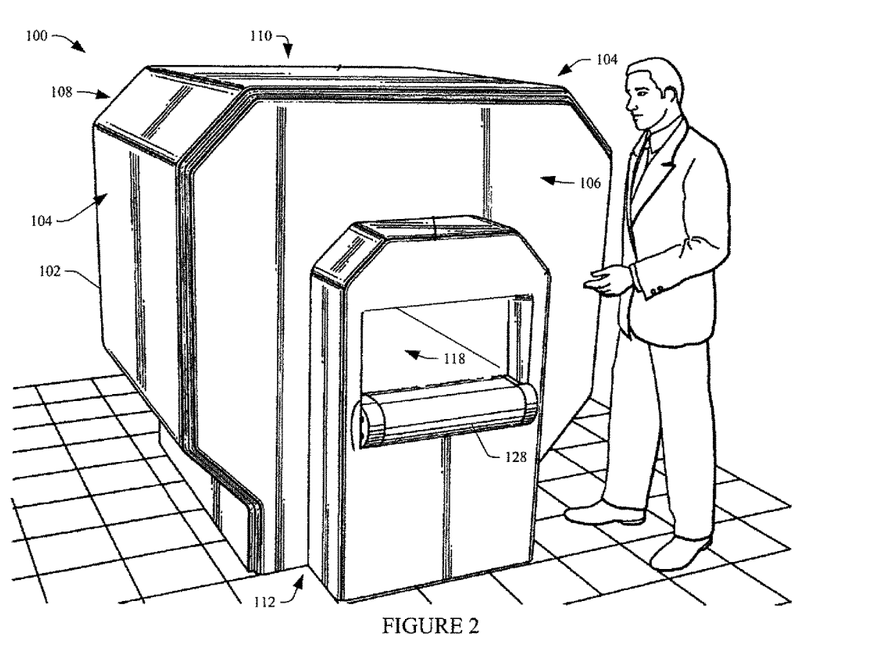
FIG. 2 schematically illustrates a front perspective view of the example inspection system.

FIGS. 1 and 2 schematically illustrate an example inspection system 100. FIG. 1 shows a perspective view from a side of the inspection system 100, and FIG. 2 shows a perspective view from a front of the inspection system 100. The illustrated inspection system 100 is an object (e.g., luggage, baggage, etc.) inspection system, for example, an inspection system at an airport checkpoint and/or other location. In another instance, the inspection system 100 includes a non-destructive testing and/or other inspection system.

The inspection system 100 includes a physical housing 102 with mechanically connected opposing sides 104, a front 106, a back 108, a top 110 and a bottom 112. The bottom 112 rests on a floor of an inspection room or area. The housing 102 houses at least a transport apparatus 114 and an imaging system 116. In one instance, the housing 102 mechanically supports at least a sub-portion of the transport apparatus 114. In another instance, the housing 102 provides a shell that surrounds the transport apparatus 114 and the transport apparatus 114 includes or rests on legs, a table, and/or other support.

The transport apparatus 114 includes an inspection system entrance port 118, a loading region 120, an inspection region entrance 121, an inspection region 122, an inspection region exit 123, an unloading region 124, an inspection system exit port 126, and a mover 128, which extends across the regions 120, 122, and 124. As described in greater detail herein, the loading and unloading regions 120 and 124 include moving X-ray attenuating curtains. Generally, the moving X-ray attenuating curtains are deployed vertically between objects and fill an inner dimension of the loading and unloading regions 120 and 124 when transporting the object to and from the inspection region 122, and are lifted at the inspection region entrance 121 and at the inspection system exit port 126, which mitigates X-ray leakage out of the entrance and exit ports 118 and 126.

As further described below, the X-ray attenuating curtains move in coordination or synchronization with the mover 128. As such, the object and/or container supporting the object do not physically contact the X-ray attenuating curtains, but instead form X-ray shielding compartments around each object. In one instance, this mitigates object jams in the transport apparatus 114 due to physical contact between an object and/or a container supporting the object and a static X-ray attenuating curtain, which causes the object and/or the container supporting the object to move. Although, it is possible that a curtain may touch an object. Also described below, a pair of X-ray attenuating curtains which form an X-ray shielding compartment around an object on the loading side and a corresponding pair of X-ray attenuating curtains which form an X-ray shielding compartment around the same object on the unloading side can be coded with a same unique coding (e.g., a visual marking), which may facilitate a user with identifying when the object of the user has been inspected and is available to be retrieved.

The imaging system 116 is located proximate the inspection region 122. The imaging system 116 includes a source 130, such as an X-ray tube, that emits ionizing radiation, such as X-ray radiation, that traverses the inspection region 122, and an X-ray detector 132 that detects radiation traversing the inspection region 122 and generates signals indicative thereof. The imaging system 116 further includes hardware and/or software for controlling the imaging system 116, processing the signals, and/or generating images of the inspection region based on the signals.

Figure 10:
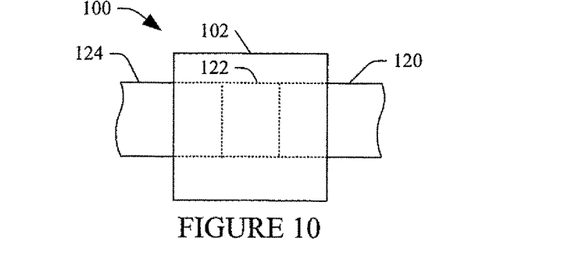
FIG. 10 schematically illustrates an example of the inspection system in which the transport system extends outside of the housing.

A computer 134, which includes a microprocessor and physical memory, controls an operation of the inspection system 100, including controlling the transport apparatus 114 to move an object to and from the inspection region 122, controlling deployment and lifting of the X-ray shielding curtains, scanning the object, displaying an image of the object via a display monitor, etc. Further description of an inspection system can be found in U.S. Pat. No. 7,072,434 B1, filed Jan. 15, 2004, entitled "Carry-on baggage tomography scanning system," and assigned to Analogic Corporation, the entirety of which is incorporated herein by reference. Other inspection system configurations are also contemplated herein. FIG. 10 shows a variation in which the loading and unloading regions 120 and 124 of the transport system 114 extend outside of the housing 102.

Figure 3:
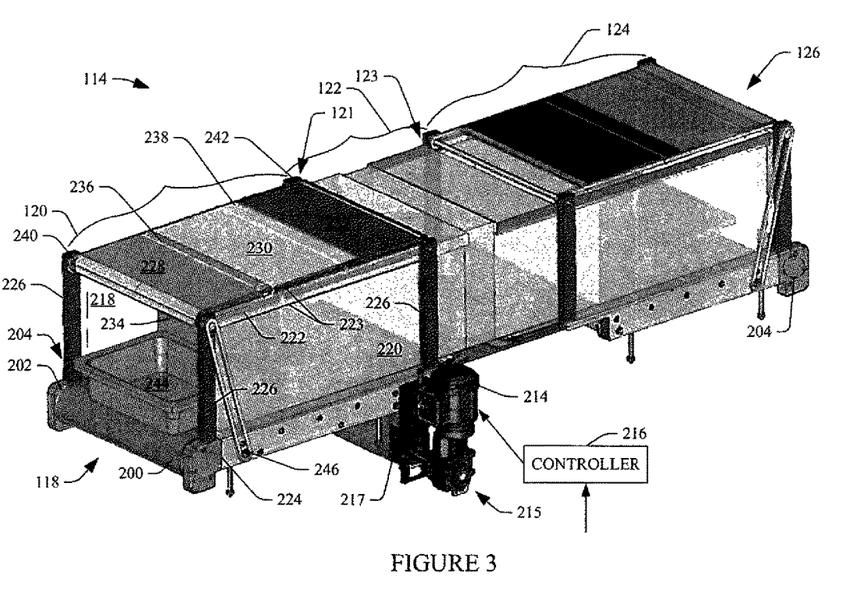
FIG. 3 schematically illustrates a transport apparatus of the inspection system.

Turning to FIG. 3, a non-limiting example of the transport apparatus 114 is illustrated. The loading and unloading regions 120 and 124 are substantially similar with respect to structure, and differ in that the loading region 120 moves an object to the inspection region 122 and the unloading region 124 moves the object from the inspection region 122. As such, only the loading region 120, and not the unloading region 124, is described in detail below for sake of brevity and clarity. One of ordinary skill in the art will recognize that the unloading region 124 can be constructed and/or operates in a similar manner to the loading region 120.

The mover 128, in this example, includes a conveyor mechanism such a conveyor belt 200 or the like. A first conveyor roller 202 resides at the inspection system entrance port 118 of the loading region 120 of the transport apparatus 114. A second conveyor roller 204 resides at the inspection system exit port 126 of the unloading region 124 of the transport apparatus 114. The first and second rollers 202 and 204 are separated by a non-zero distance that spans the loading region 120, the inspection region 122, and the unloading region 124. The loading region 120 is located at the inspection region entrance 121 at a first side of the inspection region 122, and the unloading region is located at the inspection region exit 123 at a second, opposing side of the inspection region 122.

The conveyor belt 200 extends from the roller 202 to 204, looping around outer perimeter surfaces of the first and second rollers 202 and 204. An inner side of the conveyor belt 200 physically contacts the outer perimeter surfaces of the rollers 202 and 204. The conveyor belt 200 and the rollers 202 and 204 are configured such that rotating at least one of the rollers 202 and 204 in a first direction guides the conveyor belt 200 to translate in a first direction (e.g., from the entrance port 118 to the exit port 126), and rotating at least one of the rollers 202 and 204 in a second opposing direction guides the conveyor belt 200 to translate in a second opposing direction (e.g., from the exit port 126 to the entrance port 118).

A motor 214 drives a drive system 215, which rotates a roller 217 that contacts the belt 200, and, through friction, provides movement of the belt 200. The drive system 215 can include a belt, a chain, a gear, or the like, which transfers rotational motion of a rotating shaft of the motor 214 to the roller 217, which is in frictional contact with the belt. In a variation, the motor 214 is next to one of the rollers 202 and 204 or is designed as part of the roller and the shaft is coupled directly (or indirectly through a coupling) to the one of the rollers 202 and 204 to rotate the one of and hence both of the rollers 202 and 204. In another variation, the system could contain individual conveyor segments, each with a separate drive motor. A controller 216 controls the motor 214, e.g., in response to a command signal from the computer 134.

In the illustrated embodiment, the loading region 120 is surrounded by at least three sides 218, 220, and 222. The sides 218 and 220 have a non-zero height and a non-zero length, are affixed to support members 224 at sides of the mover 128, and extend vertically or generally perpendicular to the mover 128. In the illustrated embodiment, the sides 218 and 220 extend between support posts 226 along the long axis of the mover 128, and the posts 226 extend generally vertically or generally perpendicular from the support members 224. The side 222 is a top side that is affixed to top regions of both of the sides 218 and 220, and spans across the mover 128. At least three sides 218, 220, and 222 form a tunnel and include an x-ray attenuating material such as lead or the like. In another embodiment, the loading region 120 may include more sides that form the tunnel.

The top side 222 extends between rollers 240 and 242. A curtain mover 223 (e.g., a conveyor or the like) is similar to and moves in a manner similar to the conveyor belt 200. For example, the curtain mover 223 extends from the roller 240 to 242, looping around the outer perimeter surfaces of the first and second rollers 240 and 242. An inner side of the curtain mover 223 physically contacts the outer perimeter surfaces of the rollers 240 and 242. The curtain mover 223 and the rollers 240 and 242 are configured such that rotating at least one of the rollers 240 and 242 in a first direction guides the curtain mover 223 to translate in a first direction, and rotating at least one of the rollers 240 and 242 in a second opposing direction guides the curtain mover 223 to translate in a second opposing direction.

A plurality of non-rigid (i.e., flexible) curtains, each with an x-ray attenuating material such as lead or the like, is affixed to the curtain mover 223. The curtains can be single continuous sheets or include multiple strips. In the illustrated embodiment, four such curtains 228, 230, 232, and 234 are shown in connection with the loading region 120. In another embodiment, the curtain mover 223 includes more or less curtains. Each of the curtains 228-234 includes a first end 236 (only one, for curtain 230, is illustrated for clarity) that is affixed to the curtain mover 223 and a second free moving end 238 (only one, for curtain 230, is illustrated for clarity).

Each curtain, while traversing along the top side 222, lies generally flat on the curtain mover 223, where the curtain mover 223 is a complete sheet. The curtains 228, 230 and 232 are shown as such. In response to the end 236 moving around the roller 240 from outside of the tunnel to inside of tunnel, the curtain 230 is gradually pulled (via gravity) into a position in which the free moving end 238 falls towards the conveyor belt 200 and the curtain 230 hangs vertically from the curtain mover 223 to the conveyor belt 200. The curtain 234 is shown hanging in a full x-ray attenuating or shielding position, filling the entire opening in the tunnel. Such a position is one in which the curtain blocks all or substantially all X-rays from leaking out of the transport apparatus 114 through the entrance and exits 118 and 126.

In response to the end 236 moving around the roller 242 from inside of the tunnel to outside of tunnel, the curtain 230 is gradually lifted or pulled back up to lie flat on the curtain mover 223 again. Where the curtain mover 223 is not a complete sheet, each curtain, while traversing along the top side 222, may lie flat on none or a portion of the curtain mover 223 and/or slides on the top side 222. An example of a non-complete sheet includes a variation in which the curtains 228, 230, 232, and 234 are held by a rod with the ends of the rod being supported by a linkage or chain that is moving. In this case, in response to the end 236 moving around the roller 242 from inside of the tunnel to outside of tunnel, the curtain 230 is gradually lifted or pulled back up to lie on the curtain mover 223 and/or the top side 222 again.

Figure 4:
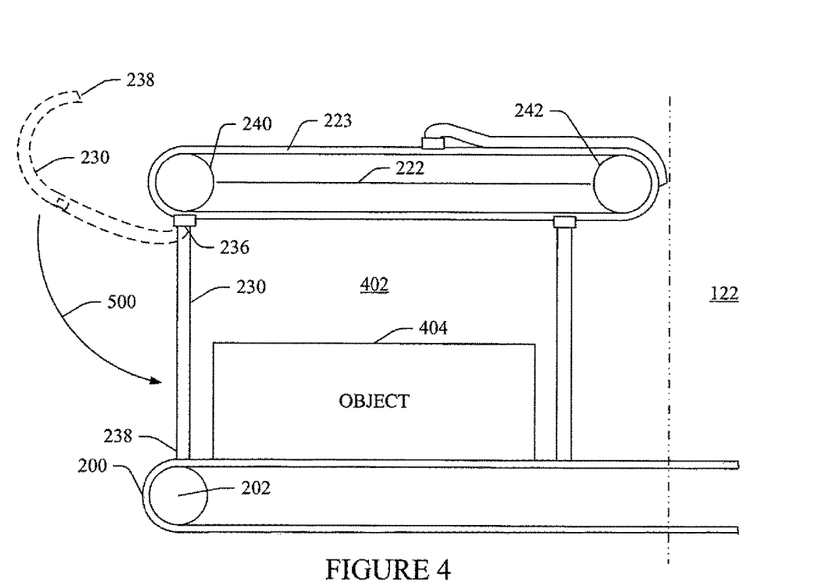
FIG. 4 schematically illustrates an example curtain configuration of the inspection system.
Figure 5:
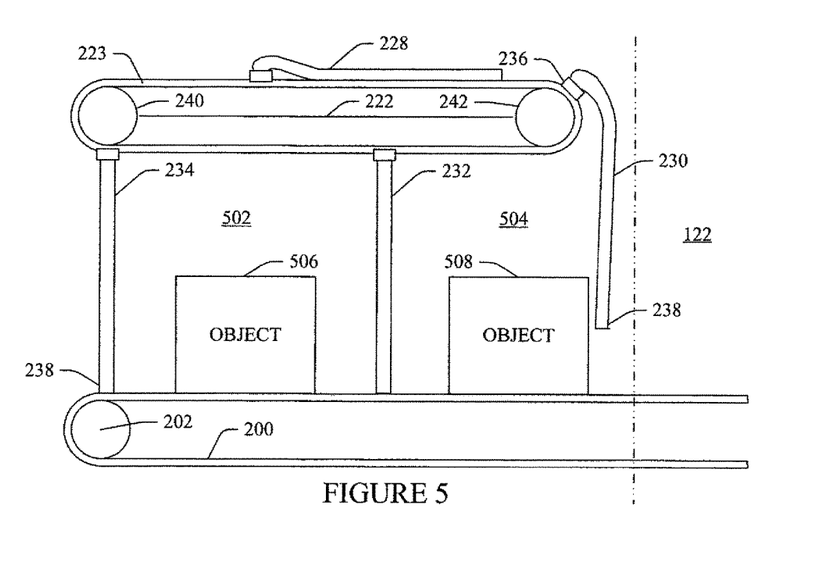
FIG. 5 schematically illustrates another example curtain configuration of the inspection system.

FIGS. 4 and 5 illustrate the above. FIG. 4 includes a three curtain configuration, and FIG. 5 includes a four curtain configuration. Other embodiments include more or less curtains. FIG. 4 shows the curtain 230 moving 500 from the top of the top side 222 to a position in which it hangs vertically towards conveyor belt 200 as the end 236 moves from outside of the tunnel to inside of the tunnel. FIG. 5 shows the curtain 230 moving from the position in which it hangs vertically towards conveyor belt 200 to the top side 222 as the end 236 moves from inside of the tunnel to outside of the tunnel. The curtain 228 represents the neighboring curtain that was pulled up before the curtain 230 and the curtains 232 and 234 are curtains that have been deployed and hang vertically.

FIG. 4 includes a single object area 402 supporting an object 404, and FIG. 5 includes two distinct object areas 502 and 504 with respective objects 506 and 508. Other embodiments include more or less object areas. The number of curtains determines a maximum number of individual areas available. Lengths of the conveyor belt 200 and the curtain mover 223 and the numbers of curtains define a size of each of the areas. The area 402, 502 or 504, in general, has a size that allows a cargo bin 244 (FIG. 3) or object to fit between two successive curtains without the curtains for the area physically contacting the bin 244, the object, and/or an item in the bin 244. In a variation, the area 402, 502 or 504 has a size that allows a predetermined size of a largest and/or longest object for inspection to fit between two successive curtains, without either curtain physically contacting the item.

At any given moment in time, for one of the areas 402, 502 or 504, at least one of the curtains is in a full x-ray attenuating or shielding position, and another of the curtains is on the top side 222. In FIG. 5, curtains 232 and 234 are in full x-ray attenuating or shielding position, and curtain 230 is not, as X-rays can traverse the region between the end 238 of the curtain 230 and the conveyor belt 200. By having at least one curtain always in the full x-ray attenuating or shielding position, X-ray leakage from the inspection region 122 out of the entrance port 118 of the tunnel is mitigated. The rollers 202 and 240 are driven such that the curtains in FIGS. 4 and 5 will move in coordination or synchronization with the conveyor belt 200. In this manner, the curtains never traverse or physically contact the object in the areas 402, 502 or 504.

In a variation, there are one or more intermediate curtains or strips within a compartment 402, 502, or 504. The one or more intermediate curtains or strips can provide additional X-ray shielding.

Figure 6:
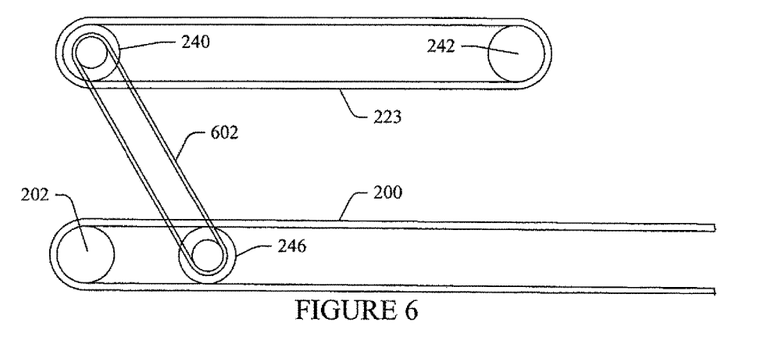
FIG. 6 schematically illustrates an example curtain moving configuration of the inspection system.
Figure 7:
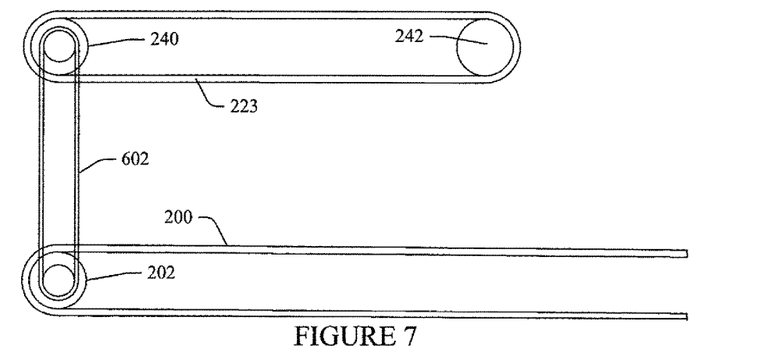
FIG. 7 schematically illustrates another example curtain moving configuration of the inspection system.
Figure 8:
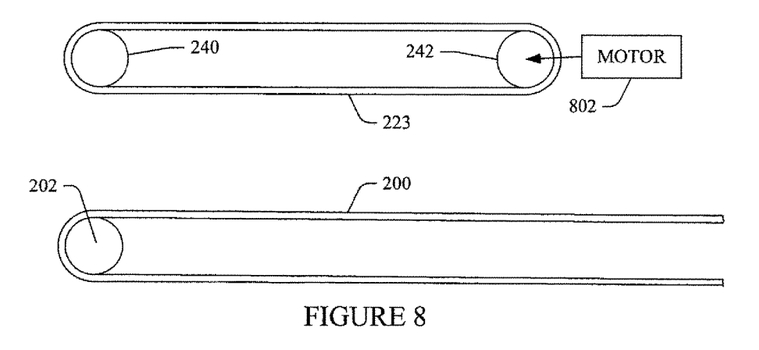
FIG. 8 schematically illustrates yet another example curtain moving configuration of the inspection system.

With reference to FIG. 3 and FIG. 6, the roller 240 is rotated indirectly by the motor 214. By way of non-limiting example, a linkage 602 such as a belt, chain or the like extends between the roller 240 and a rotatable actuator 246 that translates linear motion of the conveyor belt 200 into rotational motion, which is used, through the linkage 602 to rotate the roller 240, and, hence, translates the top side 222. In a variation, the actuator 246 is omitted and the linkage 602 extends between the rollers 240 and 202 as shown in FIG. 7. In another variation, as shown in FIG. 8, a second motor 802, which is different from the motor 214, is used to independently rotate the roller 240. In this variation, the drive systems are synchronized so that the rollers 240 and 202 are driven in coordination or synchronization. In yet another instance, the roller 240 can be otherwise rotated and/or the roller 242 can be additionally or alternatively rotated.

Returning to FIG. 3, the curtains, in one non-limiting instance, can be coded, for example, with color, gray scale, a graphic, a sign, a symbol, an alpha numeric character(s), audio, and/or other identifying feature. In such an embodiment, the user observes the coding corresponding to the area supporting their object and then can readily determine when their object is or is about to be available to be retrieved by identifying the same coding at the unloading side of the inspection system.

Figure 9:
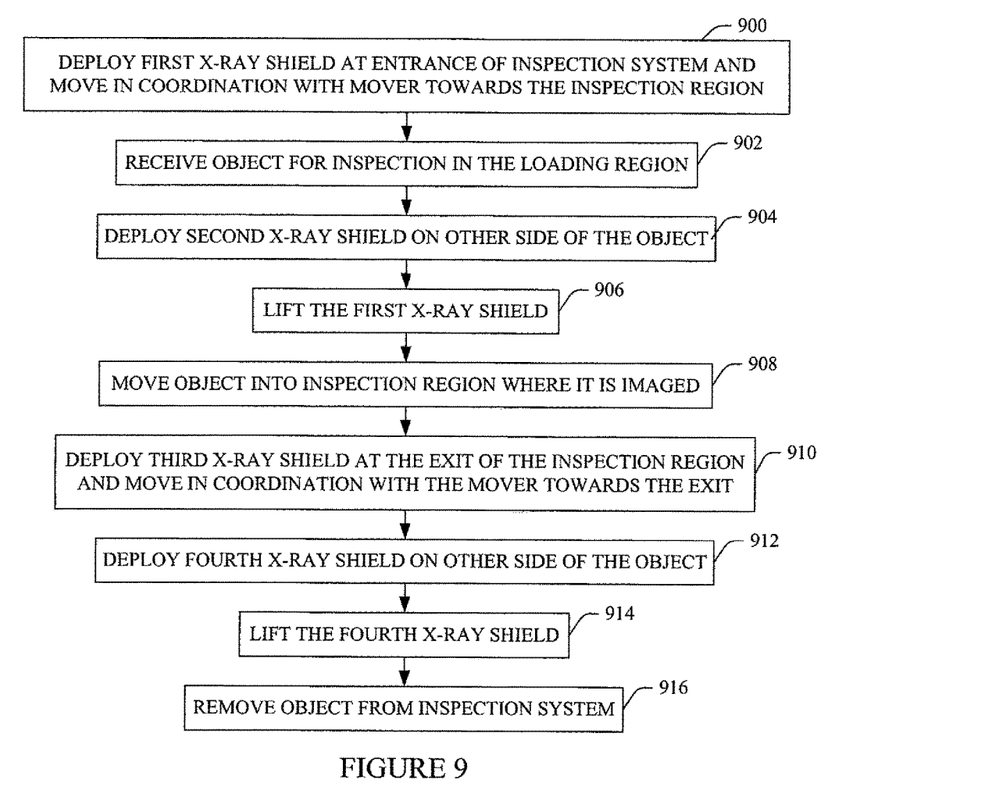
FIG. 9 illustrates an example method in accordance with the embodiments disclosed herein.

FIG. 9 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 900, a first X-ray attenuating curtain is deployed vertically at the entrance port 118 of the inspection system 100 and moves in coordination with the mover 128 towards the inspection region 122.

At 902, an object for inspection in received in the loading region 120, with the first X-ray attenuating curtain between the object and the inspection region.

At 904, as the object and the first curtain move toward the inspection region 122, a second X-ray attenuating curtain is deployed vertically at the entrance port 118, forming an X-ray attenuating compartment around the object.

At 906, the first X-ray attenuating curtain is lifted and moved out of the loading region 120 at the entrance 121 of the inspection region 122.

At 908, the object is moved into the inspection region where it is imaged.

At 910, a third X-ray attenuating curtain is deployed vertically at the exit 123 of the inspection region 122, and the mover 128 and the third X-ray attenuating curtain are moved in coordination, moving the object out of the inspection region and into the unloading region 124.

At 912, as the object and the third curtain move toward the inspection system exit port 126, a fourth X-ray attenuating curtain is deployed vertically at the inspection region exit 123, forming an X-ray attenuating compartment around the object.

At 914, the third X-ray attenuating curtain is lifted and moved out of the unloading region 124 at the exit 123 of the inspection system 100.

At 916, the object is removed from the inspection system 100.

In the above, there is always at least one X-ray shielding curtain in the full shielding position in the loading tunnel and in the unloading tunnel, which mitigates X-ray leakage from the inspection system through the transport system.

Similar to a rotating door, the user would place an object in the area before the next curtain is deployed vertically, which then closes that area, forming a radiation shielded compartment.

The methods described herein may be implemented via one or more processors executing one or more computer readable instructions encoded or embodied on computer readable storage medium which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A transport apparatus of an X-ray inspection system, comprising:
    an inspection region with an entrance and an exit;
    a loading region disposed at the entrance of the inspection region, the loading region, including:
        a first set of X-ray attenuating curtains, and
        a first curtain mover that moves the curtains of the first set of X-ray attenuating curtains into and out of the loading region between areas that support objects for inspection; and
    a conveyor device that moves an object for inspection residing in one of the areas from the loading region to the inspection region for inspection,
    wherein a pair of curtains for an area of the conveyor device that support objects for inspection is uniquely coded.

2. The transport apparatus of claim 1, wherein the first curtain mover moves the curtains by deploying the X-ray attenuating curtains to extend vertically in the loading region and lifting the X-ray attenuating curtains out of the loading region.

3. The transport apparatus of claim 1, the loading region, further comprising:
    a first side extending vertically;
    a second side extending vertically, wherein the first and second sides are on opposite sides of the conveyor device;
    a third side affixed to top regions of the first and second sides and spanning across the conveyor device.

4. The transport apparatus of claim 3, where the combination of the first, the second and the third sides forms an X-ray attenuating tunnel over the conveyor device.

5. The transport apparatus of claim 3, further comprising:
    first and second rollers separated by a non-zero distance, each of the first and second rollers extending between the first and second sides, spanning across the conveyor device; wherein the first curtain mover loops around the first and second rollers, wherein rotating at least one of the rollers translates the top side.

6. The transport apparatus of claim 5, each of the curtains, comprising:
    a first end and a second end, wherein the first end is statically attached to the first curtain mover and the second end is free to move, the first ends of at least two neighboring curtains are separated by a non-zero distance, and the curtains move with the first curtain mover.

7. The transport apparatus of claim 5, further comprising:
    a first motor that drives the conveyor device.

8. The transport apparatus of claim 7, wherein the conveyor device includes an actuator, and further comprising:
    a linkage between at least one of the first and second rollers and the actuator, which converts translational motion of the conveyor device to rotational motion of the at least one of the mover first and second rollers, wherein the first motor drives the first curtain mover through the linkage.

9. The transport apparatus of claim 7, wherein the conveyor device includes at least two conveyor rollers, and further comprising:

a linkage between at least one of the first and second rollers and at least one of the conveyor rollers, wherein the first motor drives the first curtain mover through the linkage.

10. The transport apparatus of claim 7, further comprising:
a second motor that drives the first curtain mover, wherein the first and second motor are different motors.

11. The transport apparatus of claim 1, where the first curtain mover moves the curtains in coordination with movement of the conveyor device.

12. The transport apparatus of claim 1, where the first curtain mover moves the curtains so that the curtains do not traverse the areas of the conveyor device that support objects for inspection.

13. The transport apparatus of claim 1, further comprising:
an unloading region (124) disposed at the exit of the inspection region, the unloading region, including:
a second different set of X-ray attenuating curtains, and
a second curtain mover, which moves the curtains of the second set of X-ray attenuating curtains into and out of the unloading region between inspected objects,
wherein the conveyor which moves the objects from the inspection region to the unloading region.

14. A method, comprising:
deploying a first X-ray attenuating shield between an object receiving area in a loading region and an entrance of an inspection region;
translating the first X-ray attenuating shield in coordination with the object receiving area;
receiving an object to inspect in the object receiving area;
deploying a second X-ray attenuating shield on an opposing side of the object receiving area;
translating the first and second X-ray attenuating shields in coordination with the object receiving area of an object loading region;
removing the first X-ray attenuating shield; and
moving the object to inspect into an inspection region where the object is scanned with an imaging device,
wherein the pair of the first and the second X-ray attenuating shields are uniquely coded.

15. The method of claim 14, wherein at least one X-ray attenuating shield is always deployed between the loading region and the inspection region.

16. The method of claim 14, deploying, comprising:
moving the first X-ray attenuating shield from a first location at which the first X-ray attenuating is on a top side of an X-ray attenuating loading tunnel to a second location at which the first X-ray attenuating shield is inside of the X-ray attenuating loading tunnel.

17. The method of claim 16, deploying, further comprising:
allowing a free end of the first X-ray attenuating shield to move into a vertical position in the X-ray attenuating loading tunnel in response to moving the X-ray attenuating shield into the loading tunnel.

18. The method of claim 14, comprising:
deploying a third X-ray attenuating shield between the inspection region and an unloading region;
translating the third X-ray attenuating shield in coordination with the object receiving area;
deploying a fourth X-ray attenuating shield on an opposing side of the object receiving area and in the unloading region;
translating the third and fourth X-ray attenuating shields in coordination with the object receiving area; and
removing the third X-ray attenuating shield for retrieval of the object.

19. The method of claim 18, wherein at least one X-ray attenuating shield is always deployed between the inspection region and the unloading region.

20. The method of claim 18, deploying, comprising:
moving the third X-ray attenuating shield from a third location at which the third X-ray attenuating shield hangs vertically inside of an X-ray attenuating unloading tunnel to a fourth location at which the third X-ray attenuating shield rests on a top side of the X-ray attenuating unloading tunnel.

21. The method of claim 20, deploying, further comprising:
pulling a free end of the third X-ray attenuating shield onto top side of the X-ray attenuating unloading tunnel.

22. The method of claim 18, wherein the pair of the third and the fourth X-ray attenuating shields is uniquely coded.

23. An X-ray inspection system, comprising:
a transport apparatus that moves an object from a loading region through an X-ray inspection region to an unloading region, in which a set of moving X-ray attenuating curtains, which moves in synchronization with the object, always blocks X-ray generated by an X-ray source at the X-ray inspection region from leaving the loading region and the unloading region wherein the set of moving X-ray attenuating curtains includes a pair of uniquely coded X-ray attenuating curtains.

* * * * *

UNITED STATES PATENT AND TRADEMARK OFFICE
CERTIFICATE OF CORRECTION

PATENT NO. : 10,210,960 B2
APPLICATION NO. : 15/114206
DATED : February 19, 2019
INVENTOR(S) : Patrick Splinter and Steven Weed Page 1 of 1

It is certified that error appears in the above-identified patent and that said Letters Patent is hereby corrected as shown below:

In the Specification
Column 1, Line 7, change "Jan. 31, 2014" to --Jan. 31, 2014,--

Signed and Sealed this
Twenty-sixth Day of March, 2019

Andrei Iancu
*Director of the United States Patent and Trademark Office*